United States Patent [19]

Gotzmer, Jr.

[11] 4,219,490
[45] Aug. 26, 1980

[54] FERROCENYL THIOESTERS

[75] Inventor: Carl Gotzmer, Jr., Accokeek, Md.

[73] Assignee: The United States of America as represented by the Secretary of the Navy, Washington, D.C.

[21] Appl. No.: 39,059

[22] Filed: May 14, 1979

[51] Int. Cl.² .............................................. C07F 15/02
[52] U.S. Cl. ................................................ 260/439 CY
[58] Field of Search .................. 260/439 CY, 429 CY

[56] References Cited

U.S. PATENT DOCUMENTS

| 2,810,737 | 10/1957 | Haven | 260/439 CY |
| 3,387,009 | 6/1968 | Bublitz et al. | 260/429 |
| 3,394,157 | 7/1968 | Bublitz | 260/439 |
| 4,000,172 | 12/1976 | Fachinetti et al. | 260/429 R |

OTHER PUBLICATIONS

Chemical Abstracts 52, 14580e (1958).
Chemical Abstracts 59, 7558a (1963).
Chemical Abstracts 76, 127125u (1972).
Knox et al., J. Chem. Soc. pp. 692–696 (1958).
Chemical Abstracts 77, 126813a (1972).
Chemical Abstracts 63, 18146g (1965).
Chemical Abstracts 87, 53432v (1977).
Chemical Abstracts 52, 18361e (1958).
Chemical Abstracts 80, 146269t (1974).

*Primary Examiner*—Helen M. S. Sneed
*Attorney, Agent, or Firm*—R. S. Sciascia; A. L. Branning; R. D. Johnson

[57] ABSTRACT

Ferrocenyl thiols of the formula

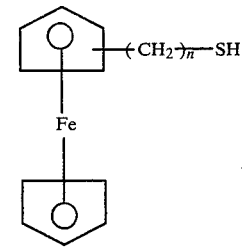

wherein n is an integer of from 2 to 4 are prepared by reacting a compound of the formula

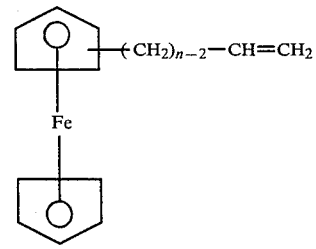

with thioacetic acid,

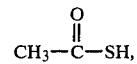

at elevated temperatures in the presence of a free radical initiator to produce a thiol ester of the formula

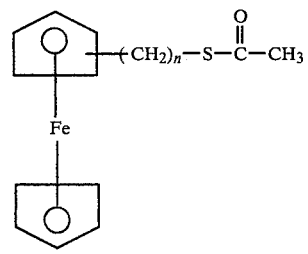

and then hydrolyzing the thiol ester to produce the thiol. The thiols are useful as non-migrating burning rate modifiers for unsaturated rubber-based propellants.

3 Claims, No Drawings

FERROCENYL THIOESTERS

BACKGROUND OF THE INVENTION

This invention relates to thiols and more particularly to ferrocenyl thiols.

Unsaturated polymers such as polybutadienes and polyurethanes are frequently used as propellant binders. Ferrocene has frequently been used as a burning rate modifier in those propellants. Ferrocene, however, tends to migrate within the propellants, resulting in an uneven distribution of ferrocene and thus uneven burning of the propellant. This problem will be eliminated if the ferrocene is bound in some way to the polymer backbone of the propellant binder.

Thiols readily enter into free radical addition reactions with olefins to produce stable products. See for example Organic Reactions, volume 13, (John Wiley and Sons, Inc., New York, 1963) pp. 165-190. The free radical addition of ferrocenyl thiols to the carbon-carbon double bonds of the polymers is one method by which the ferrocenyl group can be bound to the polymer.

G. R. Knox and P. L. Paulson (J. Chem. Soc. 1958, p. 692) demonstrated that ferrocene thiol can be prepared in three steps from ferrocene, via sulfonation, conversion of the resultant monosulfonyl chloride with lithium aluminum hydride. They reported that the thiol could never be obtained completely pure because of the extreme ease with which it was oxidized to the corresponding diferrocenyl disulfide. Another problem is that steric hinderance makes it more difficult to introduce ferrocene thiol in a polymer backbone.

SUMMARY OF THE INVENTION

Accordingly, one object of this invention is to provide novel compounds.

Another object of this invention is to provide pure ferrocene thiols.

A further object of this invention is to provide a means for preventing burning rate modifiers from migrating in propellants.

These and other objects of this invention are accomplished by providing compounds of the formula

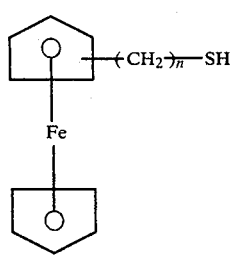

wherein n is an interger of from 2 to 4 by reacting a compound of the formula

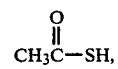

with thioacetic acid, $$CH_3\overset{O}{\underset{\|}{C}}-SH,$$

at elevated temperatures in the presence of a free radical initiator to produce a thiol ester of the formula

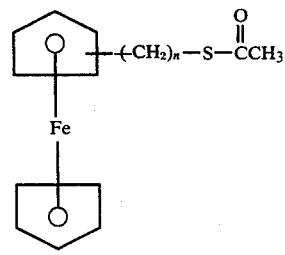

and then hydrolyzing the thiol ester to produce the thiol. The ferrocene thiols are useful as burning rate modifiers for propellants and react with unsaturation (carbon-carbon double bonds) in propellant binders to eliminate migration.

DETAILED DESCRIPTION OF THE PREFERRED EMBODIMENT

The reaction sequence for preparing the novel ferrocenyl thiols of the present invention may be depicted as follows:

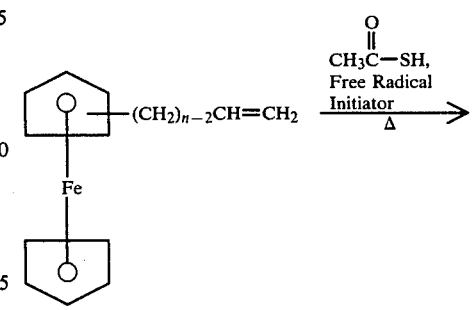

[I]

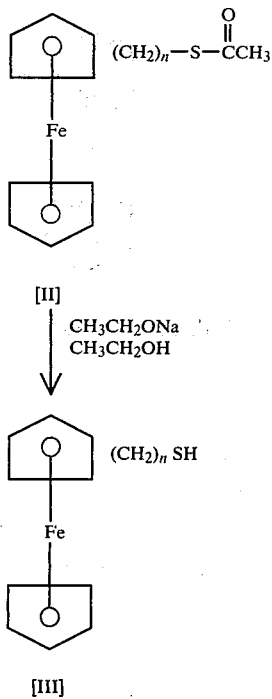

wherein n is an interger of from 2 to 4.

In the first step, thioacetic acid is reacted with an alkenyl substituted ferrocene [I] such as vinyl ferrocene, allyl ferrocene, or 3-butenyl ferrocene, to produce the corresponding ferrocenyl thioacetates [II]:
1-ferrocenyl-2-thioacetoxy ethane,
1-ferrocenyl-3-thioacetoxy propane, or
1-ferrocenyl-4-thioacetoxy butane.

The reaction is carried out at an elevated temperature (e.g., 90° C.) in the presence of a conventional free radical initiator such as 2,2'-azobis(2-methylpropionitrile). Inert aromatic solvents, such as benzene, may be used as the reaction medium.

In the second step, conventional means are used to hydrolyze the thioacetate [II] to form the thiol [III]:
2-ferrocenyl ethanethiol,
3-ferrocenyl propanethiol, or
4-ferrocenyl butanethiol.

Example 3 illustrates typical reaction conditions for this step.

Polymers containing olefinic groups (e.g., polydienes such as polybutadiene and polyurethanes made from hydroxy-terminated polybutadiene prepolymers) are often used as binders in propellants. The thiols of the present invention provide a convenient means by which ferrocenyl groups may be grafted onto these olefinic binders by free radical addition. This is based on the fact that thiols readily enter into free radical addition reactions with olefins to produce stable products. See for example Organic Reactions, Volume 13 (John Wiley and Sons, Inc., New York, 1963), pp 165–190. In this manner, non-migrating burning rate modifiers may be added to the binders.

The general nature of the invention having been set forth, the following examples are presented as specific illustrations thereof. It will be understood that the invention is not limited to these specific examples but is susceptible to various modifications that will be recognized by one of ordinary skill in the art.

EXAMPLES

Vinyl ferrocene was received from Research Organic/Inorganic Corporation and purified by the following method:

Ten grams of "vinyl ferrocene as received" was dissolved in 50 ml of benzene and placed on top of 1" I.D.×2' silica gel (Fisher, Grade 12, 28–200 mesh) column and eluted with benzene. The first orange colored band eluted off the column ($R_f$ value 0.92 in benzene, Table I) with benzene was evaporated to dryness and characterized as vinyl ferrocene: mp 49°–50° C.; ir(CCl$_4$) 6.18μ (—CH=CH$_2$); nmr (CDCl$_3$) ppm 6.5 (m,1,—C$\underline{H}$=CH$_2$), 5.2(m,2,—CH=C$\underline{H}_2$) and 4.23 (m,9,—C$_{10}$$\underline{H}_9$).

Anal. Calcd. for C$_{12}$H$_{12}$Fe: C,67.96; H,5.70; Fe,26.33. Found: C,67.89; H,5.79; Fe,26.21.

The second orange colored band ($R_f$ value 0.055 in benzene) was eluted off the column using methanol, evaporated to dryness and characterized as °-hydroxyethyl ferrocene; mp 72°–74° C.; ir (CCl$_4$) 2.79μ(OH); nmr(CDCl$_3$) ppm 4.55(m,1,—C$\underline{H}$OH), 4.28 (m,9,—C$_{10}$$\underline{H}_9$), 1.96 (s,1,—CHO$\underline{H}$) and 1.44(d,3,C$\underline{H}_3$).

Anal. Calcd. for C$_{12}$H$_{14}$FeO: C,62.64; H,6.13; Fe,24.27. Found: C,62.71; H,6.19; Fe,24.35.

EXAMPLE 1

Attempted Preparation of 1-Ferrocenyl-2-thioacetoxy Ethane Using Irradiation

In a typical experiment 2.12g (0.01 mol) of purified vinyl ferrocene and 0.76 (0.01 mol) of thioacetic acid were dissolved in 30 ml of GC spectrophotometric quality benzene and placed in a pyrex photoreactor fitted with a fritted purging tube and reflux condenser. The solution was purged 45 minutes with helium prior and during irradiation of $1.75 \times 10^{19}$ photon/min. from a Hanovia 100 watt type SOL high pressure quartz mercury vapor lamp. No change in the infrared bands of the mercaptans (3.9μ) and vinyl groups (6.18μ) nor any product formation could be observed by thin layer chromatography during a photolysis time of up to eight hours. It was observed that photo-decomposition of vinyl ferrocene occurred (formation of dark brown precipitate) along with protection of thioacetic acid from the ultraviolet light.

EXAMPLE 2

Synthesis of 1-Ferrocenyl-2-thioacetoxy Ethane

The above procedure was repeated except for the introduction of 0.82g (0.005 mol) 2,2'-azobis (2-methylpropionitrile) prior to purging with helium and replacement of the irradiation step by heating in an oil bath at 90° C. Complete disappearance of the mercaptan (3.9μ), vinyl (6.18μ) and carbonyl groups (5.90μ) occurred in the infrared after one hour at 90° C. Product formation was followed by thin layer chromatography and infrared analysis (formation of thioester carbonyl group at 5.98μ). The reaction mixture was poured on top of a 1" I.D,×7' silica gel (Fisher, Grade 12, 28–200 mesh) column and eluted with benzene. Trace quantities of unreacted vinyl ferrocene were extracted first, followed by a second orange band ($R_f$ value 0.56 in benzene, Table 1), which was evaporated to dryness and characterized as 1-ferrocenyl-2-thioacetoxy ethane; mp 47°–48° C.; ir (CCl$_4$) 5.98μ (thioester C=O); nmr (CDCl$_3$) ppm 4.11 (m,9,—C$_{10}$$\underline{H}_9$), 3.05 (m,2,—C$\underline{H}_2$), 2.58(m,2,—C$\underline{H}_2$), and 3.34 (S,3,C$\underline{H}_3$).

Anal. Calcd for $C_{14}H_{16}FeOS$: C,58.35; H,5.60; Fe,19.38; S,11.12. Found: C,58.26; H,5.46; Fe,19.38; S,11.28.

The above procedure was scaled-up by a factor of ten to produce a sufficient quantity of 1-ferrocenyl-2-thioacetoxy ethane for further hydrolysis experiments. Purified vinyl ferrocene (21.2g) yielded 21.7g (75%) of 1-ferrocenyl-2-thioacetoxy ethane and two other uncharacterized ferrocene derivatives ($R_f$ value 0.48 and 0.19 in benzene, Table I) and totaling less than 1g.

EXAMPLE 3

2-Ferrocenyl Ethanethiol

In a typical experiment 2.0g (0.0069 mol) of 1-ferrocenyl-2-thioacetoxy ethane was dissolved in 100 ml of benzene and purged 30 minutes with nitrogen. Forty ml of 0.2N sodium ethylate in ethanol was purged 30 minutes with nitrogen and added to the above ferrocene thioester-benzene solution. The mixture was stirred for 24 hours at ambient temperature with nitrogen purging and the reaction monitored by thin layer chromatography (Table 1) and infrared analysis (disappearance of the thioester carbonyl at 5.98μ and formation of thiol at 3.90μ). Then the reaction mixture was filtered to remove a white crystalline precipitate (presumably sodium acetate) and acidified with glacial acetic acid. The mixture was filtered again to remove white crystals taking great precaution not to expose the mixture to air. The product was evaporated to dryness at 50° C. and 1 mm Hg for two hours yielding a foul smelling reddish brown oil as the final material. The oil was dissolved in nitrogen purged heptane and eluted through the previously mentioned 7' silica gel column using nitrogen purged heptane as eluant. Only one yellow band was observed, eluted under nitrogen, stripped to a reddish brown oil (1.6g, 90% yield) and characterized as 2-ferrocenyl ethanethiol: oil at 25° C.; ir (neat) 3.9μ(SH), nmr (CDCl$_3$) ppm 4.06 (m,9,C$_{10}$H$_9$) and 2.72 (m,5,(C$\underline{H}_2$)$_2$ S$\underline{H}$).

Anal. Calcd for $C_{12}H_{14}FeS$: C,58.55; H,5.73; Fe,22.70. Found: C,58.72; H,5.74; Fe,22.63.

Obviously numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. A ferrocenyl thioester of the formula

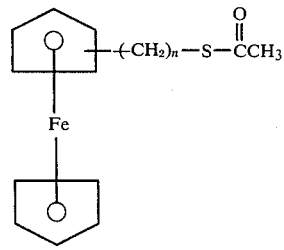

wherein n is an interger of from 2 to 4.
2. 1-ferrocenyl-2-thioacetoxy ethane.
3. 1-ferrocenyl-3-thioacetoxy propane.

* * * * *